United States Patent [19]

Kurhi

[11] Patent Number: 5,774,916
[45] Date of Patent: Jul. 7, 1998

[54] ERGONOMIC MATRIX FOR BACK ALIGNMENT

[76] Inventor: Jaakko Kurhi, 5101 San Leandro St., Oakland, Calif. 94601

[21] Appl. No.: 874,624

[22] Filed: Jun. 13, 1997

[51] Int. Cl.⁶ .................... A47C 23/00; A47C 27/14; A61F 5/02
[52] U.S. Cl. .................... 5/632; 5/633; 5/423; 5/731; 5/726; 5/922; 5/953; 128/845; 128/870; 606/240; 606/242
[58] Field of Search .................... 5/633, 630, 632, 5/732, 731, 733, 953, 421, 423, 922, 722, 636, 726; 128/845, 870, 846; 606/240, 242

[56] References Cited

U.S. PATENT DOCUMENTS

| | | | |
|---|---|---|---|
| 1,904,039 | 4/1933 | Bruder | 606/240 |
| 3,359,577 | 12/1967 | Rogers . | |
| 3,757,366 | 9/1973 | Sacher | 5/630 |
| 4,206,524 | 6/1980 | Cook | 5/630 |
| 4,230,099 | 10/1980 | Richardson . | |
| 4,254,518 | 3/1981 | Buhren et al. | 5/732 |
| 4,805,603 | 2/1989 | Cumberland . | |
| 4,923,187 | 5/1990 | Mombrinie . | |
| 4,989,591 | 2/1991 | Anders, Jr. . | |
| 5,121,961 | 6/1992 | Marshall | 5/632 |
| 5,207,704 | 5/1993 | Shields | 128/845 |
| 5,224,956 | 7/1993 | Dumas et al. | 606/240 |
| 5,279,310 | 1/1994 | Hsien | 128/845 |
| 5,337,427 | 8/1994 | Pagano et al. | 5/630 |
| 5,452,728 | 9/1995 | Iams | 5/630 |
| 5,479,667 | 1/1996 | Nelson et al. | 5/632 |

*Primary Examiner*—Alexander Grosz
*Attorney, Agent, or Firm*—Richard C. Litman

[57] ABSTRACT

Ergonomic support members formed of and contoured to a corrected spinal curvature of an individual. The matrix provides the rigid support necessary for correction of the spinal curvature by gradual realignment with continued use of the support members, and may have channels for optional forced air flow, for heating and cooling and comfort of the individual during sleep or rest. Each support member is closely contoured to have a concave cross-section dimensioned according to the serial cross sections of a respective body section (e.g. head, shoulders, thorax, pelvis, and legs) while laying supine. The resulting contour of the support member thus provides the necessary convexity to evenly distribute body weight along the entire longitudinal axis of the spine and thereby provide corrective support for the spinal curvature. In the transverse plane, the contour forms a snug concavity wrapping up the sides of an individual. The concavity is symmetrical through the longitudinal axis so that the weight of a misaligned body section gradually exerts force upon the vertebra to torsionally realign, which force continues until the body weight is evenly distributed across the surface of the concavity, and thus ultimately alleviates pain in the misaligned areas. A removable head support member allows traction to be placed on the cervical vertebrae. Several embodiments of the support member are described.

18 Claims, 7 Drawing Sheets

ERGONOMIC MATRIX FOR BACK ALIGNMENT

BACKGROUND OF THE INVENTION

1. FIELD OF THE INVENTION

The present invention relates to a support member for aligning a human spinal column. More particularly, the form includes a rigid matrix resistant to deformation by body weight, which is molded to provide a symmetric cavity closely simulating the contours of a well-aligned human back, into which an individual with a misaligned back lies to allow the force of gravity to gradually conform the back to the contours of the form.

2. DESCRIPTION OF RELATED ART

The human spinal column is a series of vertebrae interspaced by cartilaginous discs, the vertebrae further including foramen through which nerves pass to enervate the rest of the body. Thus, these nerves are susceptible to impingement between the disc or vertebrae, resulting in pain. Such impingement can be caused by compression or pinching, particularly when any portion of the spinal column is disrupted, such as by trauma, (both acute and repetitive), arthritis, and aging, resulting in movement of the disc or vertebra from its normal position in the spinal column.

Moreover, even slight malalignments of the spinal column, though not permanent or injurious to the nerves, may cause the body to react in spasm of the overlying muscles, such as the paraspinous complex, in an effort to protect the nervous system from damage. In either case, the ailing individual feels pain.

Therefore, the art is replete with inventions which address the need to alleviate back pain, including support members having specific features and contours intended to support the vertebrae in a prone or supine position, in an effort to realign the spine along its original spinal curve (including the lumbar, thoracic and cervical curves). For example, U.S. Pat. No. 3,359,577 issued December 1967 to Rogers describes a one-piece, back support device for engaging the back of a user, the support device having an arched profile (convex/concave in transverse planes) including a shoulder supporting portion and a lumbar region supporting portion. A cradling effect of the shoulder portion and the concave surface assists the user in finding a proper resting position, whereas the transverse convex surface aligns the spine, once the proper resting position has been found. The device provides a skeletal, vertically ribbed construction, preferably made of a plastic, molded one-piece construction, which provides a relatively rigid support of sufficient strength to support the user without flexing or otherwise changing shape.

Another similar device is shown in U.S. Pat. No. 4,230,099 issued October 1980 to Richardson, describing a device for aligning the spine, having two elongated ridge members with a curve corresponding to the natural lumbar and thoracic curves of the human spine. A user lies on the supporting surface with the spine substantially aligned between the ridge members. In U.S. Pat. No. 5,279,310 issued January 1994, Hsien describes a tri-partite spinal column correction device, each part contoured for receiving one of the head, lumbar or leg regions, using hook and loop fasteners to join each part together in a series from head to toe, whereafter inflation chambers are adjusted to adapt the invention to the curve of the spine of the user. Although the Hsien invention teaches that variously contoured devices can be linked in series, neither the Richardson, Rogers nor the Hsien inventions describe features which allow signifi-

2 cant longitudinal readjustment of the support members for traction and longitudinal alignment of the spine, unlike the present invention.

However, the art does include devices which are able to exert mild traction along the longitudinal axis of the spine, such devices being contoured to grasp the external body features of the user to achieve this effect. U.S. Pat. No. 4,805,603 issued February 1989 to Cumberland describes a cervical traction pillow having a receiving pocket for engaging the head divided from a receiving surface for the shoulders by an expansion slot. The slot is widened by an inflatable air sac to exert traction on the neck of a user. Such inflatable air sac is a complicated means, requiring a hand pump, and may be a costly means, of accomplishing such objective. The present invention provides a much simpler mechanism, reducing material cost and complexity. Moreover, the Cumberland patent teaches only cervical traction and fails to teach full body support during normal sleeping or resting to gradually realign the spine.

Less relevant structures showing combined features generally related to the art of support members are described in the following patents. U.S. Pat. No. 5,479,667 issued January 1996 to Nelson et al. describes a dual ergonomic pillow which is contoured for reclining both supine as well as on one's side, having a cutout for the shoulder and arm. An audio transmitter and speakers are also included internally within the head support member. U.S. Pat. No. 5,452,728 issued September 1995 to Iams describes a set of supportive pivots which serve as a fulcrum on which the spinal column can be self-manipulated by exercising thereon while the spine is supported in an unloaded state, either prone or supine. U.S. Pat. No. 4,989,591 issued February 1991 to Anders, Jr. describes a somewhat pyramidal, orthopedic appliance for prone positioning useful in aligning the spine and femorae. U.S. Pat. No. 4,923,187 issued May 1990 to Mombrinie describes a radiolucent (i.e. x-ray transparent) iliac crest support, having a pair of adjustable oblong pillows attached by removable fasteners to a rigid, flat sheet. U.S. Pat. No. 4,206,524 issued June 1990 to Cook describes a supporting structure made of sponge-like padding for relieving pressure on bony areas, particularly in the area of decubitus ulcers. An air pump and tubing for passing a gas to an enlarged vent opening below an ulcerated area to accelerate healing is provided. U.S. Pat. No. 5,337,427 issued August 1994 to Pagano et al. describes a contoured, rocking birthing board. Unlike the present invention, each of the above noted inventions fail to teach features which address the need for mild traction to longitudinally decompress the spine in an unloaded state, and, more fundamentally, fail to show a suitably rigid matrix which direct forces downward through the spinal column for accomplishing the purposes described herein.

Therefore, none of the above inventions and patents, taken either singularly or in combination, is seen to describe the instant invention as claimed. Thus, an ergonomic matrix and, support member for back alignment solving the aforementioned problems and addressing the aforementioned needs is desired.

SUMMARY OF THE INVENTION

Accordingly, it is a principal object of the invention to provide a support member having a rigid, inflexible matrix which is symmetrically contoured to closely match the body contours of an individual and provide therein a curvature which corresponds to a corrected spinal curvature for support and longitudinal realignment of the spine.

It is another object of the invention to provide a multi-part support member for longitudinally applying traction to the spine.

It is a further object of the invention to provide a simple structure for applying traction between a cervical support member and the thoracic and lumbar support members.

Still another object of the invention is to provide an internal cooling and heating system flowing through the matrix.

Yet another object of the invention is to provide multi-part contoured support members which, while rigidly supporting the spine in a corrective manner, allow coordinated, pivotable adjustment of the parts to permit seated and partially reclined positions.

The present invention accomplishes each of these objectives by providing one or more support members each formed of a rigid, inflexible matrix, contoured to a corrected spinal curvature of an individual. The matrix is inflexible and rigid so that the weight of a misaligned body section gradually exerts force upon the vertebra (through its respective muscle groups and attachments) to torsionally realign the spinal column, which force continues until the body weight is evenly distributed across the surface of the concavity, and thus ultimately alleviates pain in the misaligned sections. Thus, suitably rigid materials (such as PVC or ABS plastics, fiberglass, wood, etc) and methods of construction, later described, are used to achieve this primary objective.

Each support member is closely contoured to have a concave cross-section dimensioned according to the serial cross sections of a respective body section (e.g. head, shoulders, thorax, pelvis, and legs) while laying supine. The resulting contour of the support member thus provides the necessary convexity along its longitudinal axis to evenly distribute body weight along the entire longitudinal axis of the spine and thereby provide corrective support for the spinal curvature. In the transverse plane, the contour forms a snug concavity symmetrical through the longitudinal axis, thereby defining a left wall and a right wall wrapping up the sides of an individual. These walls act to redirect the downward forces acting on the sides of an individual more centrally through a supine body, thus aiding in the torsional correction of the spinal column.

In an alternative embodiment, the matrix provides connected interstitial spaces, or open cells, which provide the rigid support necessary for correction of the spinal curvature by gradual realignment over time with continued use of the support members. The open cells also optionally provide channels for forced air flow, for heating and cooling and comfort of the individual during sleep or rest.

Several other embodiments of the support member are also described. Each of two additional embodiments include a pair of interactive, separate components to provide spinal traction, namely a head support member and a trunk support member. The head support member is contoured with a deepened pocket for receiving the occiput of the head and thus defines a promontory supporting the neck and serving as a ledge pressing anteriorly on the occiput when an anteriorly directed pulling force is applied to the head support member. The trunk support member is unitary with lumbar support sections and defines a cutout in each of the left and right walls below the armpits, which provides space for placement of the arms when supine.

In the first additional embodiment the head support member is attached by hook and loop type fasteners directly onto a flat portion of the trunk support member extending below the head. The hook and loop type fasteners are positioned on the undersurface of the head support member and the top surface of the flat portion to allow longitudinal adjustment of the head support member on the flat portion. Thus, during supine rest with the head support cradling the head, the contours of the trunk support member and unitary lumbar sections anchor the shoulders, torso, pelvis and legs and resist longitudinal movement of the lower body; a previously detached head support member can therefore be repositioned by pulling anteriorly to exert mild traction upon the cervical spine and thereupon be reattached to the flat portion, thereby fixing traction.

In the second additional embodiment, one support member is provided with studs dimensioned to removably engage a channel, which may be formed by a one or more connected matrix cells, in the other support member, each stud depending longitudinally either from the head or trunk support member. By adjusting the depth of engagement of the stud within a channel, the head support member can be adjusted longitudinally and be used to exert traction upon the cervical spine.

Yet another embodiment includes a body-length support member having most or all of the above features. The contoured surface of the body-length support member evenly supports the body, thus distributing its weight over the entire matrix with the resulting effect of minimizing unconscious body movement during sleep resulting from otherwise felt regional pressure against the body.

Ancillary features of the present invention include a bed frame which supports the body-length unitary matrix, thereby allowing it to stand alone as a piece of bedroom furniture. For comfort of the individual, the concavity may be lined with fleece, terry cloth, or other suitably absorbent and comfortable fabric. A forced-air heating or cooling apparatus can also be added, including a blower motor and ducting which channels preconditioned air into an inlet port in communication with the matrix; perforations are provided in the contoured surface for release of the conditioned forced air into the concavity, thereby allowing the conditioned air to pass over a resting individual for comfort. Likewise, electrically resistive heating elements may be internally and integrally disposed within the matrix to form a radiant heating system. Finally, a series of flexible joints may be provided in the body-length embodiments, the flexible joints positioned below the hip and knee joints of an individual, allowing the rigid matrix to flex and comfortably support an individual in a semi-reclined or seated position, further enabling embodiment of the matrix in various seats and similar furniture.

It is an object of the invention to provide improved elements and arrangements thereof in an ergonomic matrix for back alignment for the purposes described which is inexpensive, dependable and fully effective in accomplishing its intended purposes. These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

The present invention is shown throughout the Figures in its multiple embodiments as illustrative of the various combinations of features which may be alternatively or optionally included with the supportive matrix for correcting spinal alignment. Regardless of the embodiment, the present invention is directed at any of variously embodied support members which are closely contoured to have a concave cross-section dimensioned according to the serial cross sections of a respective body section (e.g. head, shoulders, thorax, pelvis, and legs) while laying supine. As suggested by FIGS. 3, 4, and 5, (showing a transverse plane of a substantially similar support member 114 of a second embodiment later described), the trunk support member 14 integrally comprises variously ergonomically contoured sections, a series of representative sections being a thoracic section 30, a lumbar section 40, and a pelvic section 50.

Figure 1:
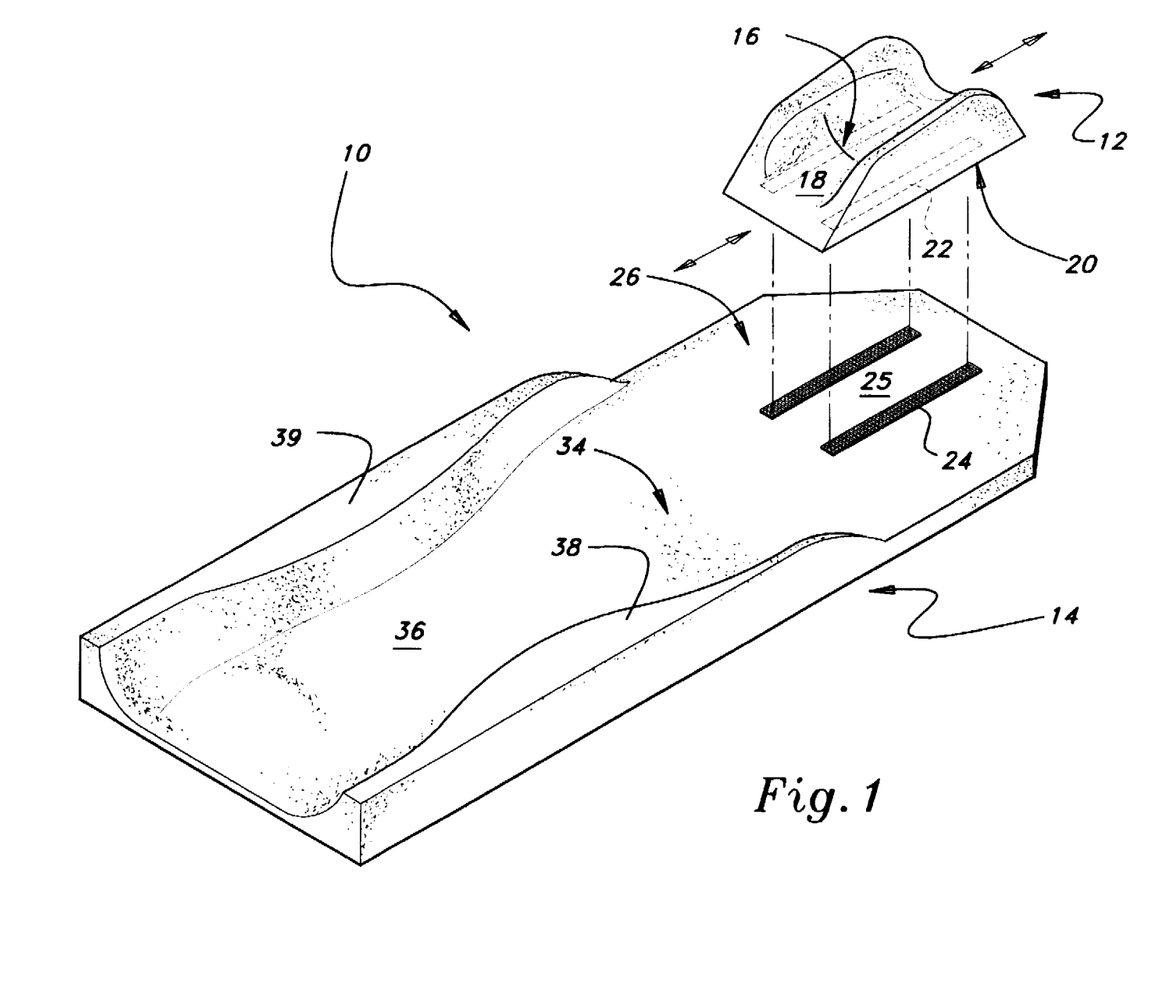
FIG. 1 is an exploded, perspective view of the preferred embodiment of the support member for back alignment according to the present invention.

The preferred embodiment 10 is shown in FIG. 1, including a head support member 12 and a trunk support member 14. The two support members 12,14 form a pair of interactive, removable components to provide cervical spinal traction (as later discussed) as well as provide spinal support for corrective alignment.

Figure 3:
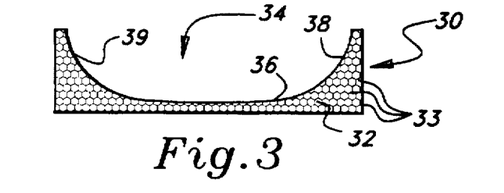
FIG. 3 is a cross-sectional view showing the concave and symmetrical contour of a thoracic section of an embodiment according to the present invention, as drawn along lines 3—3 of FIG. 2.
Figure 4:
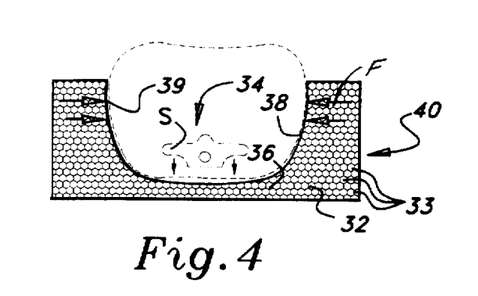
FIG. 4 is a cross-sectional view showing the concave and symmetrical contour of a lumbar section of an embodiment according to the present invention, as drawn along lines 4—4 of FIG. 2, showing a cross section of a human torso in phantom lines and effective force vectors.
Figure 5:
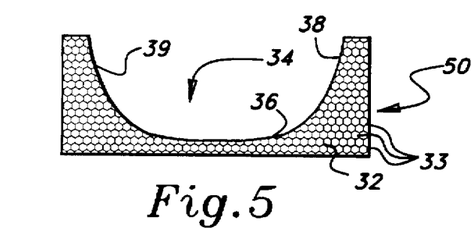
FIG. 5 is a cross-sectional view showing the concave and symmetrical contour of a pelvic section of an embodiment according to the present invention, as drawn along lines 5—5 of FIG. 2.

Each of the FIGS. 3–5 also suggest an internal construction of one of the multiple support members, being formed of a rigid, matrix 32. The matrix may comprise any lightweight, rigid material to accomplish the intended purpose of torsionally realigning the spine by allowing gravitational forces to be directed through the body and conforming it to the symmetry of one of the support members. The matrix is preferably created by using a shell or mold using known construction methods, such as by vacuum forming a flexible plastic sheet over a negative ABS mold, frequently used in boat manufacturing process, or laminating a suitable flexible sheet, such as heated PVC sheets or fiberglass fabrics, over a positive form. Using either of these methods, a support structure is created in the form of a human cast. Various sized casts can thus be made cheaply and quickly to custom order and size. The ergonomic support member may include any rigid, inflexible material and may be chosen from the group consisting of plastics including polyvinylchloride and ABS, fiberglass, wood, laminated and composite materials, and hardened foamed urethanes and plastics.

In an alternative embodiment of the matrix, the matrix 32 provides connected interstitial spaces, or open cells 33, which provide the rigid support necessary for correction of the spinal curvature. The open cells 33 also optionally provide channels for forced air flow, for heating and cooling and comfort of the individual during sleep or rest.

To permit correction of the spinal curvature, the matrix (referred to herein as matrix 32, but which should be understood to include any of the described structural materials) defines a concavity 34 which has a contour defined by a surface 36 of each section 30,40,50. The surface 36 is partially defined by a left wall 38 and a right wall 39 for wrapping the sides of an individual laying supine. As suggested in FIG. 4, these walls 38,39 are important in providing added surface area and opposing the tendency of a body to splay outwardly in order to distribute gravity forces over an otherwise horizontal surface. Thus, the side walls 38,39 act with opposing horizontal force vectors F and redirect the weight of the body more centrally through the spine S. In turn, a malaligned spine will tend to torsionally readjust to conform with the symmetry of the surface 36, as suggested by the two downward force vectors.

Momentarily referring to and as more clearly seen in FIGS. 6–8, each of the left and right walls 38,39 terminate below the armpits, which provides space for placement of the arms to the outside of the concavity 34 when resting supine. A flat portion 26 of the trunk support member 14 is a unitary and planar section which is disposed to extend below the head of an individual when supine.

Figure 2:
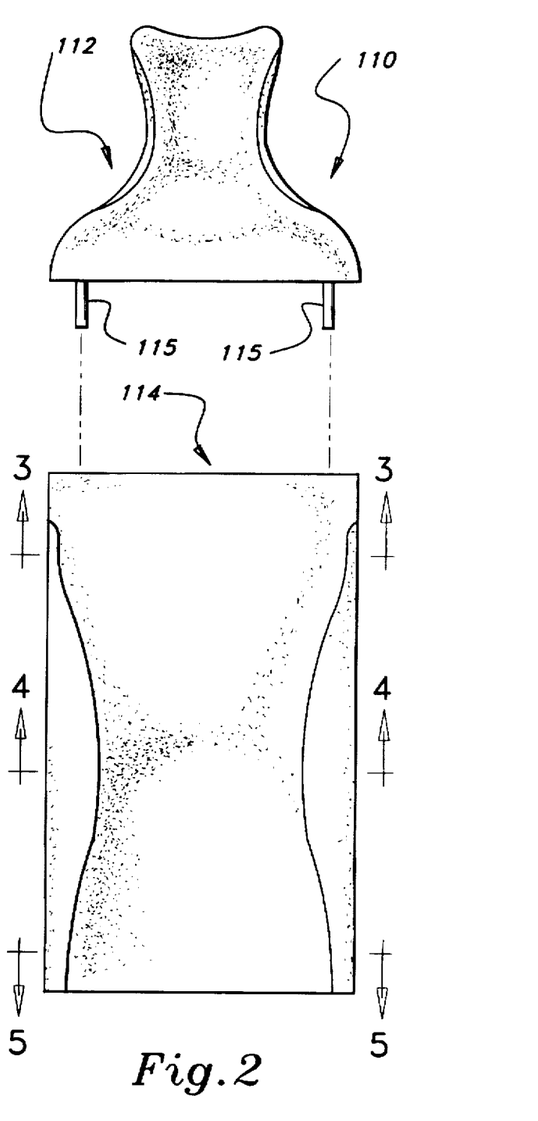
FIG. 2 is an exploded, top plan view of a second embodiment of the support member for back alignment according to the present invention.

The surface 36 defines concavity 34 corresponding to a spinal curvature of an individual at any given transverse plane; the concavity 34 must be symmetrical as viewed in the transverse plane and through the longitudinal axis of the support member, such axis being parallel with the directional arrows for sections 3, 4, and 5 of FIG. 2. The resulting contour of the support member defined by an infinite series of parallel transverse planes thus provides a necessary convexity along the entire longitudinal axis of the spine to evenly distribute body weight, and thereby provide corrective support for the spinal curvature. More specifically, the concavity 34 is symmetrical through the longitudinal axis so that the weight of a misaligned body section gradually exerts a force upon the vertebra (through its respective muscle groups and attachments) to torsionally realign the spinal column, which force continues until the body weight is evenly distributed across the surface 36 of the concavity 34. In other words, the contour should conform snugly to the body of the individual so as to be longitudinally symmetrical, and may be custom fitted to an individual.

Now referring back to FIG. 1, the head support member 12 is contoured with a deepened pocket 16 for receiving the occiput of the head and thus defines a promontory 18 for supporting the neck. Momentarily referring to FIG. 6, the promontory 118 of the second embodiment 110 better illustrates how the promontory 18 can serve as a ledge to press anteriorly on the region of the occiput O when an anteriorly directed pulling force is applied to the head support: member 12.

The head support member 12 has an underside 20 to which a first mating component 22 of complementary hook and loop type fasteners are attached. The second mating component 24 is attached to the flat portion 26 of the trunk support member 14. The hook and loop type fasteners 22,24 are positioned on the underside 20 of the head support member 12 and a top surface 25 of the flat portion 26 to overlappingly mate, allowing longitudinal adjustment of the head support member 12 on the flat portion 26. Thus, during supine rest with the head support member 12 cradling the head, the contour of the trunk support member 14 and unitary lumbar sections anchor the shoulders, torso, pelvis (and optionally legs in other embodiments) to resist longitudinal movement of the lower body. To exert traction upon the cervical spine, the head support member 12 can be detached and repositioned while the head is cradled therein, by pulling anteriorly to exert mild traction upon the cervical spine. The head support member 12 is thereupon reattached to the flat portion by realigning the mating hook and loop fasteners 22,24, thereby fixing the head support member 12 in a position which holds the neck in mild traction.

Figure 6:
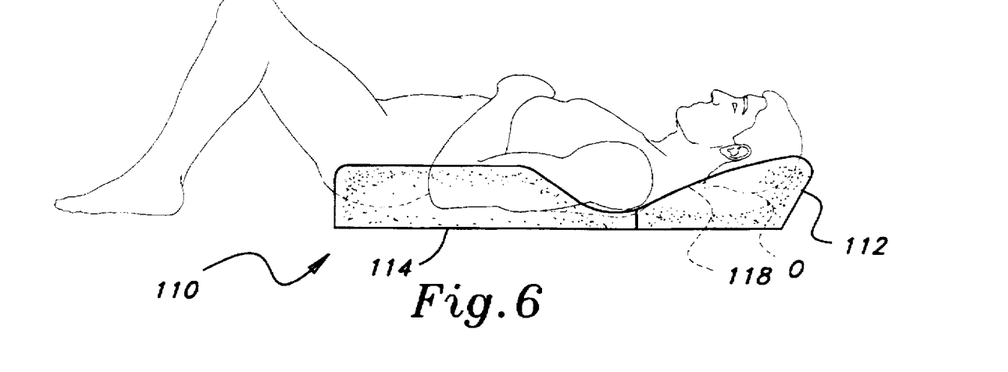
FIG. 6 is a side elevational, environmental view of the second embodiment of the support member according to the present invention, shown in use relative to the body of a supine individual.
Figure 7:
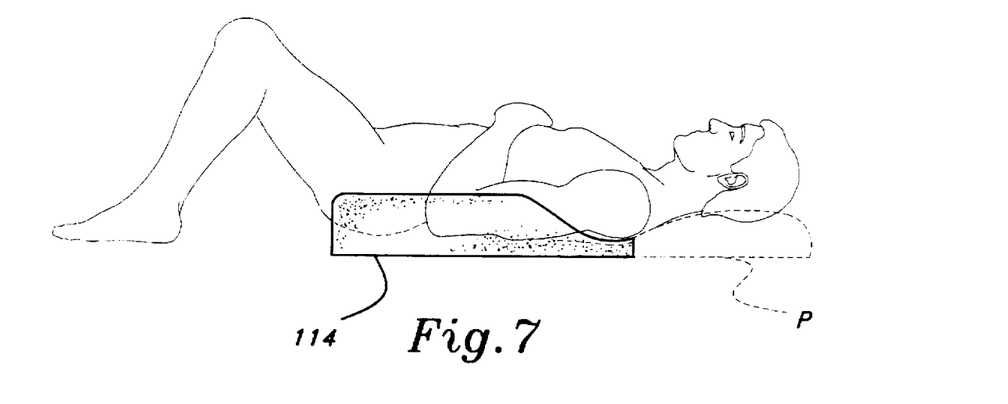
FIG. 7 is a side elevational, environmental view of the second embodiment of the support member without a head support member, shown in use with a conventional pillow and relative to the body of a supine individual.
Figure 11:
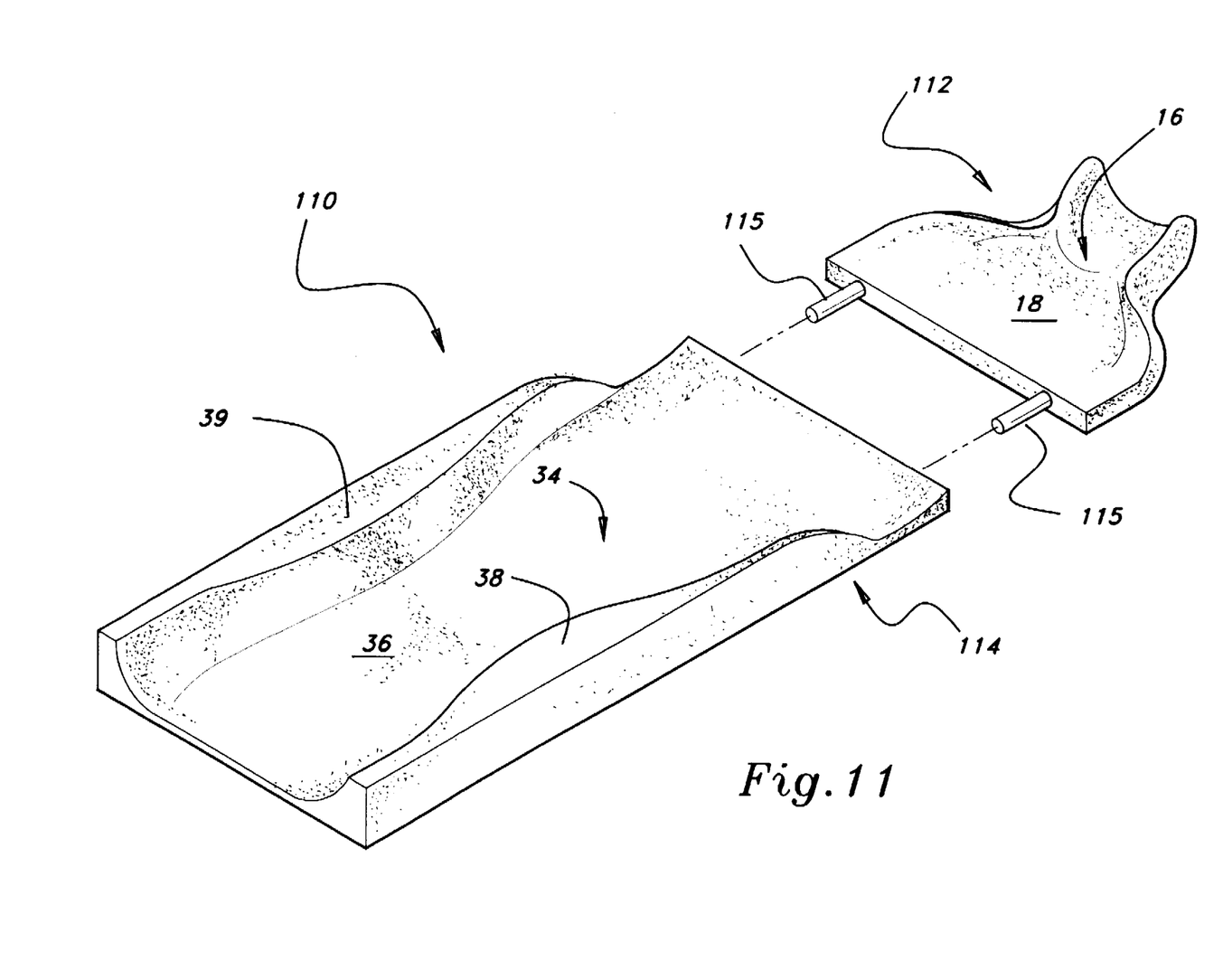
FIG. 11 is an exploded, perspective view of the third embodiment of the support member.

In a second embodiment 110 of FIGS. 2, 6 and 11, the head support member 112 is provided with studs 115 dimensioned to removably engage a channel (not shown) formed by a one or more connected matrix cells 33, which assembly serves as an alternative attachment means permitting cervical traction. Each stud 115 may depend longitudinally either from the head support member 112 or trunk support member 114, so long as a receiving channel in the other support member receives the stud 115 to align the head and trunk support members along the spinal longitudinal axis. The remaining features of the head support member 112 and trunk support member 114 having reference numerals corresponding to the features of the first embodiment 10 are functionally identical to those features of the first embodiment. Therefore, by adjusting the depth of engagement of the stud 115 within a matrix cell 33, the head support member 112 can be adjusted longitudinally and be used to exert traction upon the cervical spine. As can be appreciated from FIG. 7, the removable nature of the head support member 112 also allows the trunk support member to be used independently, allowing the use of a conventional pillow P for head support.

Figure 8:
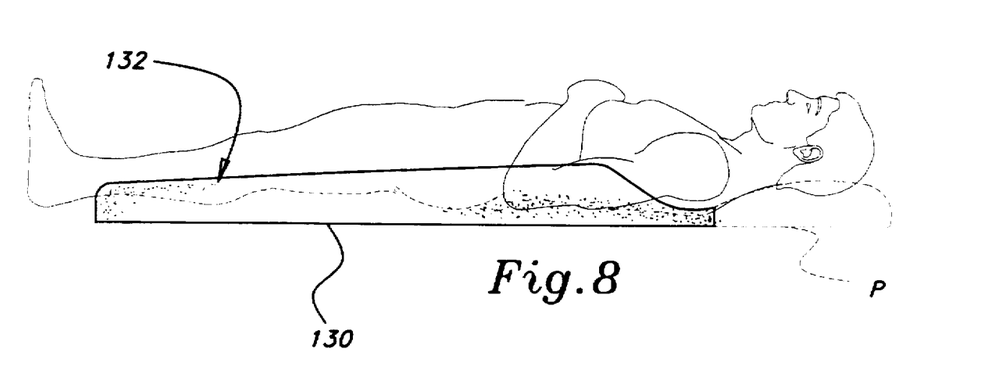
FIG. 8 is a side elevational, environmental view of a third embodiment of the support member, shown in use with a conventional pillow and relative to the body of a supine individual.

A third embodiment is shown in FIG. 8, which is a body-length support member 130 having, in addition to the above features of the trunk support member 14 or 114, an extended leg support portion 132. The leg support portion 132 is contoured to closely conform to the legs, having a contoured surface 136 of the leg support portion defined by an extension of the matrix 32 discussed above. By providing a support member which evenly supports the body, its weight is distributed evenly over the entire matrix 32 with the resulting effect of minimizing unconscious body movement during sleep resulting from otherwise felt regional pressure against the body. Thus, even for individuals with well-aligned backs, the contoured surface 136 provides an added advantage over conventional support surfaces.

Figure 9:
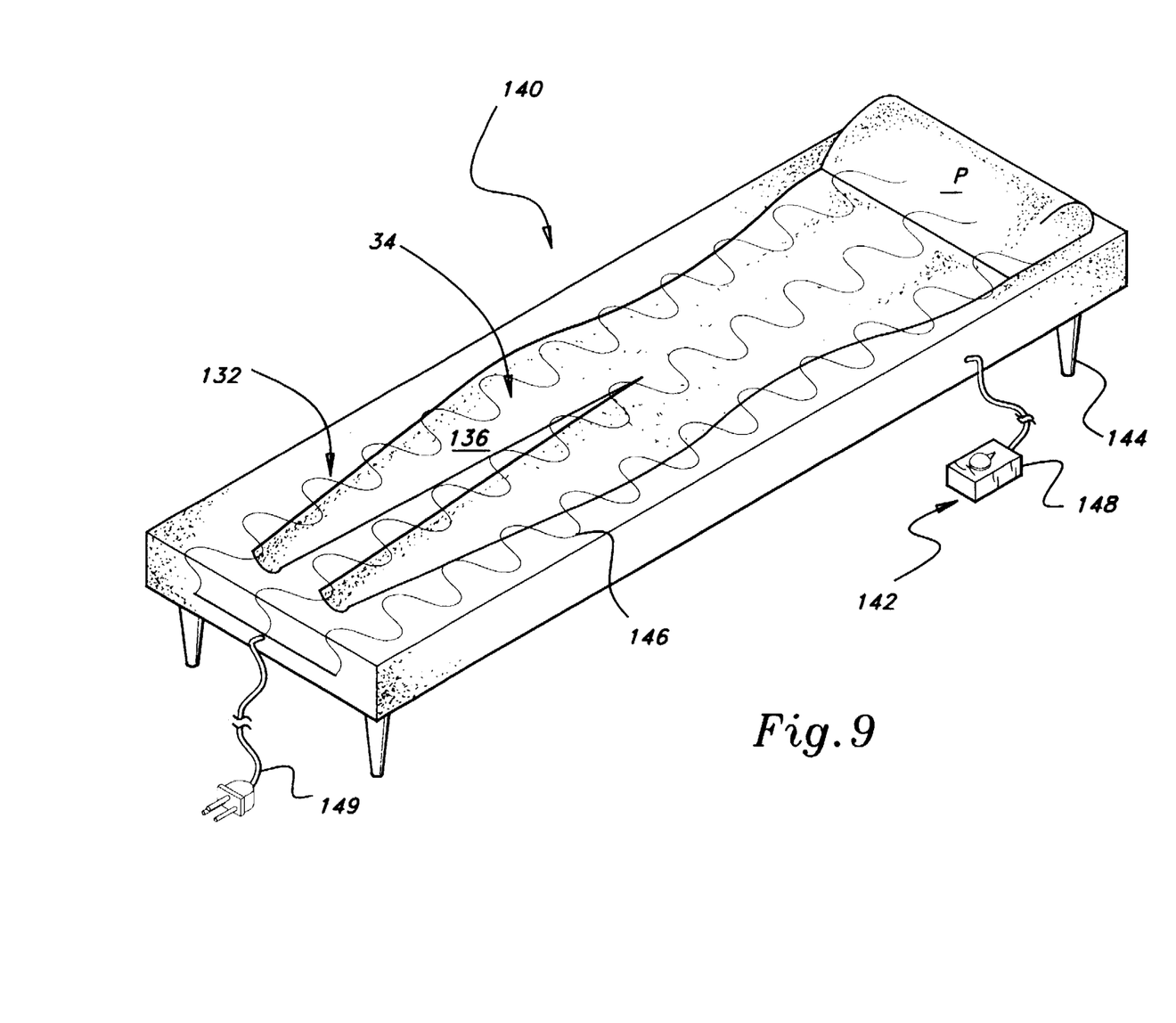
FIG. 9 is a perspective view of a fourth embodiment of the support member, shown embodied as a freestanding bed and having an integral radiant heating system.
Figure 10:
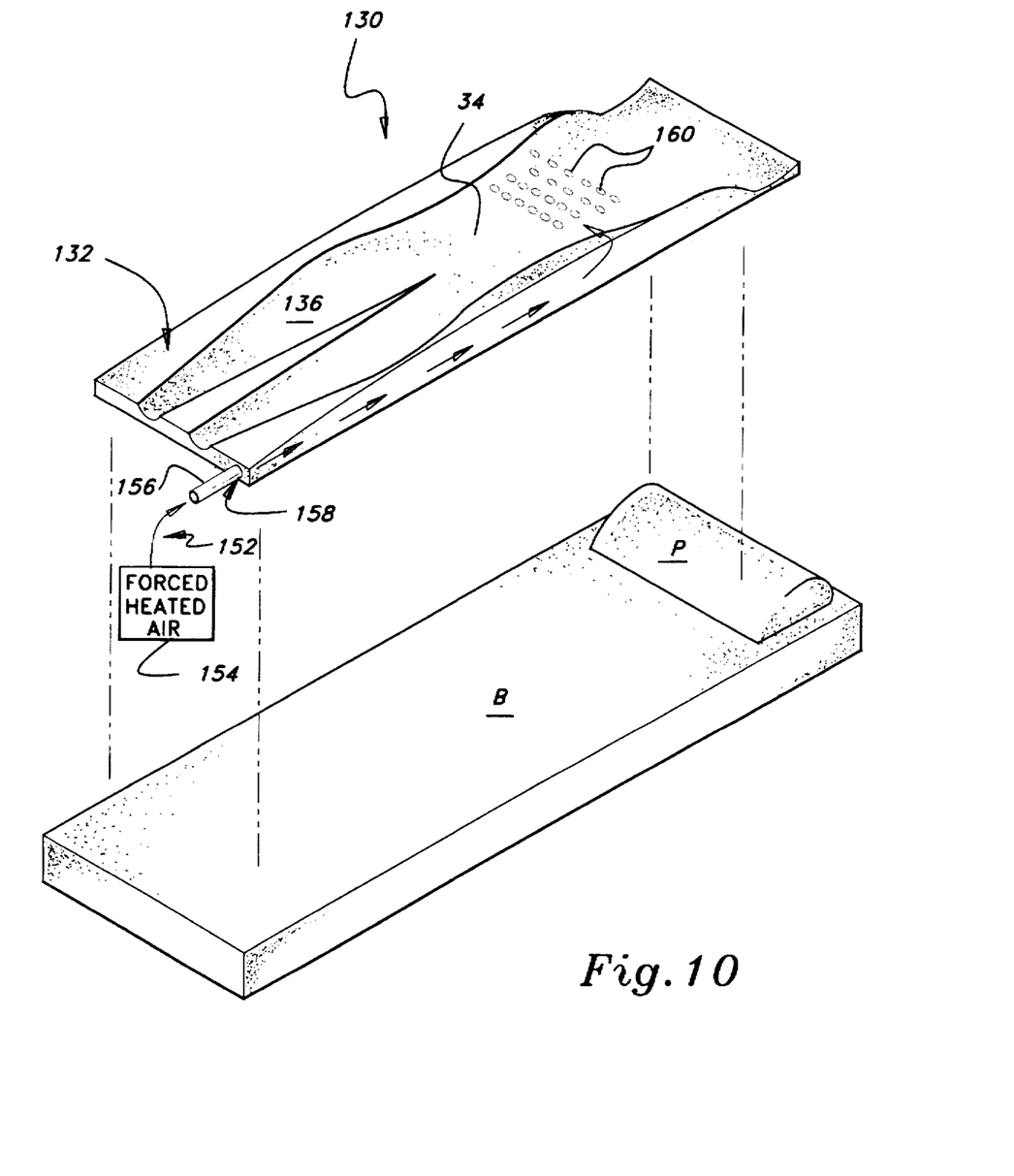
FIG. 10 is an environmental, perspective view of the third embodiment of the support member, shown modified to have an integral forced air heating system.
Figure 12:
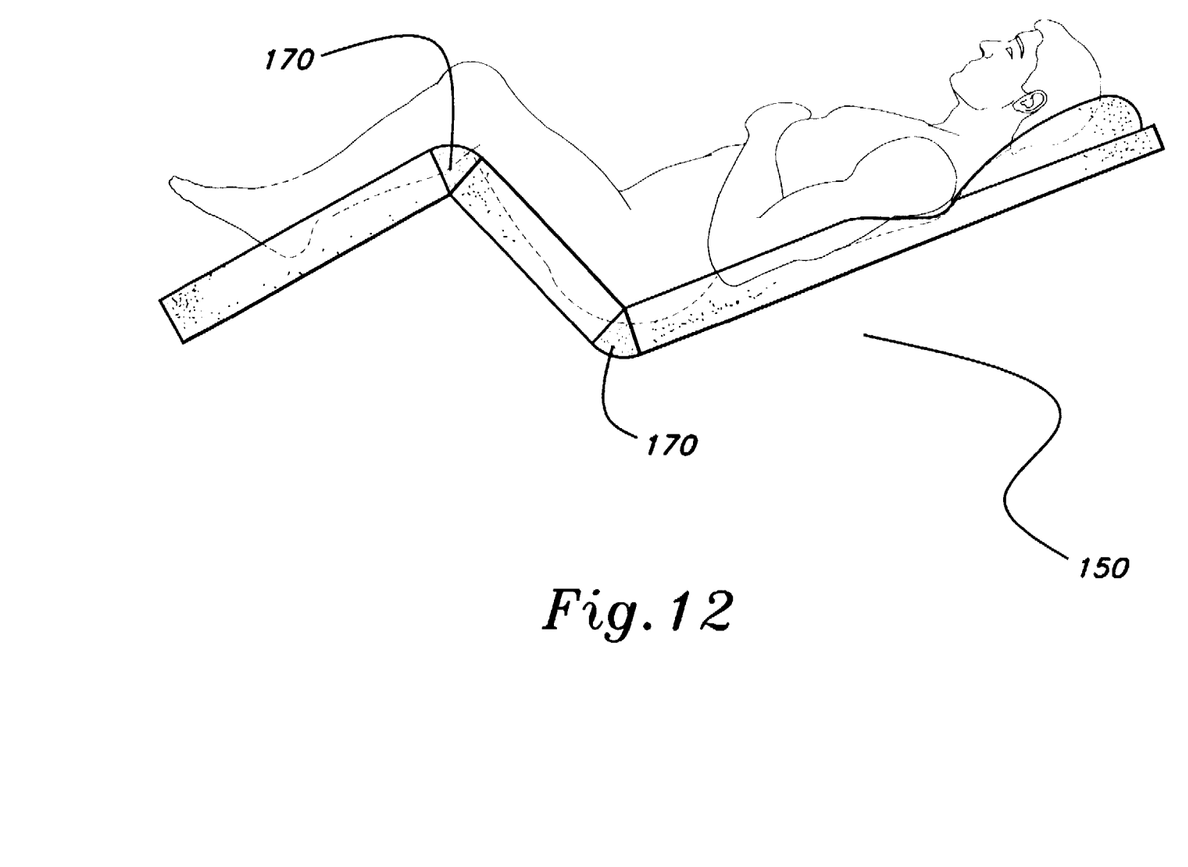
FIG. 12 is a side elevational view of a fifth embodiment of the support member adapted with flexible joints for pivotal movement of the matrix relative to the body of a supine individual illustrated in phantom lines.

As can be appreciated from FIGS. 9, 10, and 12, the body-length support member may include various versions (including a fourth embodiment 140, a modified third embodiment 130, and a fifth embodiment 150, respectively) each having a contoured surface 136 of body-length including leg support portion 132, in addition to some or all of the features described for the trunk support member 14. In FIG. 9, the fourth embodiment 140 is a body-length support member modified to include a bed frame having 4 legs 144, which frame (not shown) supports the body-length unitary matrix 140. Thus, the body-length support member can stand alone as a piece of bedroom furniture. For comfort of the individual, the concavity 34 of any embodiment may be lined with fleece, terry cloth, or other suitably absorbent and comfortable fabric (not shown).

In FIG. 10, a conventional bed B is shown with pillow P upon which the body-length support member 130 is shown as a retrofit device which is simply placed upon the bed B. Support member 130 is also modified to include an ancillary feature, namely a forced-air heating or cooling apparatus 152. The apparatus 152 includes a blower motor and heating apparatus 154 and ducting 156. The ducting 156 channels preconditioned air into an inlet port 158 in communication with the open cells and channels of the matrix 32, allowing the air to be forced into the interstitial spaces and travel throughout the matrix 32. Perforations 160 are provided in the contoured surface 136 for release of the conditioned forced air into the concavity 34, thereby allowing the conditioned air to pass over a resting individual for comfort. In FIG. 9 however, a heating apparatus 142 is provided to radiantly heat the matrix 32 of the fourth embodiment 140, including electrically resistive heating elements 146 which are internally and integrally disposed within the matrix 32. The heating elements are thermoregulated by a control unit 148 and may be powered by standard household current, as represented by the electrical plug and cord unit 149.

Finally and referring to FIG. 12, each of the body-length embodiments may be modified to include a series of flexible joints 170, each of the flexible joints 170 positioned below the hip or knee joint of an individual as shown in a representative fifth embodiment 150. The joints 170 may be manufactured of a highly compressible and resilient foamed material, such as open celled foamed rubbers or urethanes, allowing the joints to compress and resiliently return embodiment 150 to a planar configuration from the representative semi-reclined position as shown in FIG. 12. Such joints allows the rigid matrix to flex and comfortably support an individual in a semi-reclined position, as shown in phantom lines. Other pivotally hinging means can also be used in place of the foamed materials. Such feature further enables additional embodiments of the matrix to be envisioned, including various seats and similar furniture such as lawnchairs.

It is to be understood that the present invention is not limited to the embodiments described above, but encompasses any and all embodiments within the scope of the following claims.

I claim:

1. An ergonomic support member for back alignment comprising:

a rigid, inflexible support structure defining a trunk support member, having a longitudinal axis corresponding to the axis of the spine of a human individual, said trunk support member defining a cavity contoured for receiving the body of a human individual laying supine, said cavity being symmetrical through said longitudinal axis, wherein said trunk support member further defines a left wall and a right wall each for wrapping up the sides of an individual laying supine in said cavity, and wherein further said trunk support member defines a continuous surface facing said cavity, said continuous surface corresponding in shape along said longitudinal axis to the spinal curvature of the individual and thereby defining a thoracic section, a lumbar section, and a pelvic section of said trunk support member, whereby, when said continuous surface receives a supine individual, said left wall and said right wall oppose horizontal force vectors directed outward from the sides of the supine individual and redirect the weight of the body more centrally through the spine to torsionally readjust and conform the spine with the symmetry of said continuous surface.

2. The ergonomic support member for back alignment as defined in claim 1, further comprising a head support member having a deepened pocket contoured for receiving the occiput of a head of a human individual, thereby defining a ledge for abutting the occiput and supporting the neck.

3. The ergonomic support member for back alignment as defined in claim 2, wherein said head support member includes an underside and a first mating component of complementary hook and loop type fasteners attached thereto, and wherein said trunk support member includes an integrally attached flat portion dimensioned and configured to extend below the head of an individual when supine, said flat portion having a top surface and a second mating component of a hook and loop type fasteners attached thereto, said first mating component and said second mating component positioned to overlappingly mate;

whereby the head support member can be removed, adjusted along the top surface of the flat portion and reattached while the head is cradled within the head support member to exert mild traction upon the cervical spine.

4. The ergonomic support member for back alignment as defined in claim 2, further including joining means for removably attaching said head support member to said trunk support member to allow traction on the cervical spine.

5. The ergonomic support member for back alignment as defined in claim 4, wherein said joining means include at least two studs depending from one of either said head support member or said trunk support member, said remaining one of either said head support member or said trunk support member defining a receiving channel for receiving one of said studs, both said at least two studs and each said receiving channel oriented along said longitudinal axis.

6. The ergonomic support member for back alignment as defined in claim 5, wherein said support structure is formed of a rigid matrix having open cells in communication with one another, and wherein further said receiving channel is defined by at least one of said open cells, and wherein further each of said studs are dimensioned in diameter to engage said at least one open cell and dimensioned in length to permit the head support member to be incrementally adjusted longitudinally while in engagement, whereby the head support member can be used to exert traction upon the cervical spine.

7. The ergonomic support member for back alignment as defined in claim 1, wherein said support structure is formed of a rigid matrix having open cells in communication with one another.

8. The ergonomic support member for back alignment as defined in claim 7, wherein said surface of said trunk support member defines a plurality of perforations in communication with said open cells and exiting into said cavity; and wherein further said trunk support member defines an intake port in communication with said open cells, thereby forming a channel for forcing a gaseous fluid from said intake port to said plurality of perforations.

9. The ergonomic support member for back alignment as defined in claim 8, further comprising a conditioning apparatus for thermoregulating and conditioning air and subsequently forcing the conditioned air through said channel of said matrix.

10. The ergonomic support member for back alignment as defined in claim 9, wherein said conditioning apparatus includes a blower motor and ducting for channelling the preconditioned air from said blower motor into said inlet port.

11. The ergonomic support member for back alignment as defined in claim 1, further comprising radiant heating means integrally disposed within said support structure.

12. The ergonomic support member for back alignment as defined in claim 11, said radiant heating means including electrically resistive heating elements and a control unit for thermoregulating said heating elements.

13. The ergonomic support member for back alignment as defined in claim 1, said left wall and said right wall each dimensioned and configured to terminate below an armpit of an individual supinely resting in said cavity of said trunk support member, thereby forming a space for passing the arm of the individual beyond one of said walls.

14. The ergonomic support member for back alignment as defined in claim 1, further including a leg support portion integrally extending from said pelvic section of said trunk support member, said leg support portion having a cavity contoured for closely receiving the legs of an individual, thereby defining a body-length support member.

15. The ergonomic support member for back alignment as defined in claim 14, further comprising a bed frame for supporting said body-length support member.

16. The ergonomic support member for back alignment as defined in claim 13, further comprising a flexible joint for pivotally angling said body-length support member into a semi-reclined position.

17. The ergonomic support member for back alignment as defined in claim 16, wherein said flexible joint is a foamed open-celled plastic.

18. The ergonomic support member for back alignment as defined in claim 1, wherein said support structure is a rigid, inflexible material chosen from the group consisting of plastics including polyvinylchloride and ABS, fiberglass, wood, laminated and composite materials, and hardened foamed urethanes and plastics.

* * * * *